United States Patent
Reiner

[11] 4,005,073
[45] Jan. 25, 1977

[54] 6-ACYL DERIVATIVES OF AMINOPENICILLANIC ACID

[75] Inventor: Roland Reiner, Basel, Switzerland

[73] Assignee: Hoffmann-La Roche Inc., Nutley, N.J.

[22] Filed: Feb. 24, 1975

[21] Appl. No.: 552,485

[30] Foreign Application Priority Data

Mar. 12, 1974 Switzerland .................. 3415/74

[52] U.S. Cl. .......................... 260/239.1; 424/271
[51] Int. Cl.² ........................................ C07D 499/66
[58] Field of Search ............................. 260/239.1

[56] References Cited

FOREIGN PATENTS OR APPLICATIONS 1,160,211  6/1969  United Kingdom ............ 260/239.1

*Primary Examiner*—Gerald A. Schwartz
*Attorney, Agent, or Firm*—Samuel L. Welt; Bernard S. Leon; William H. Epstein

[57] ABSTRACT

Compounds represented by the following formula

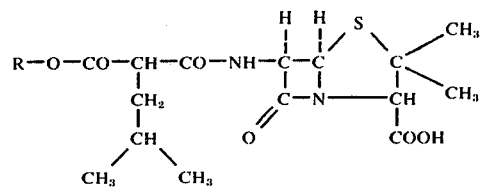

wherein R is hydrogen, lower alkanoyloxymethyl, lower alkyl, indanyl or a radical represented by the formula

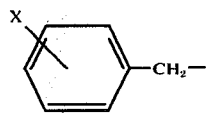

wherein X may be hydrogen, halogen, hydroxy, lower alkyl, lower alkoxy or a lower alkoxy-lower alkyl group, pharmaceutically acceptable salts and hydrates thereof. These compounds are useful as antibiotics.

4 Claims, No Drawings

6-ACYL DERIVATIVES OF AMINOPENICILLANIC ACID

DETAILED DESCRIPTION OF THE INVENTION

The present invention is directed to novel 6-acylaminopenicillanic compounds represented by the general formula

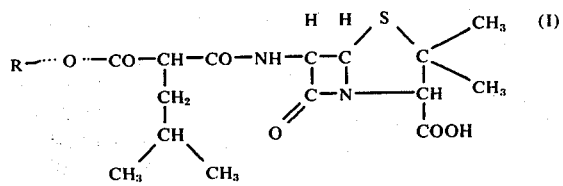

wherein R is hydrogen, lower alkanoyl-oxymethyl, lower alkyl, indanyl or a radical represented by the formula

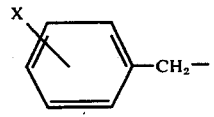

wherein X is hydrogen, halogen, hydroxy, lower alkyl, lower alkoxy or lower alkoxy-lower alkyl, pharmaceutically acceptable salts thereof and hydrates thereof.

The term "halogen" as utilized herein represents all four halogens with fluorine, bromine and chlorine being preferred.

In accordance with the present invention lower alkyl, lower alkoxy and lower alkanoyl groups can contain from 1 to 6 carbon atoms. Examples of lower alkyl groups represented by R or X in formula I above include methyl, ethyl, n-propyl and the like. Examples of lower alkoxy groups represented by X in formula I include methoxy, ethoxy and the like. Examples of lower alkoxy-lower alkyl groups represented by X in formula I are methoxymethyl, methoxyethyl, ethoxymethyl and the like. Examples of lower alkanoyloxymethyl groups represented by R include acetoxymethyl, pivaloyloxymethyl and the like.

Preferred compounds in accordance with the present invention are those compounds of formula I in which R represents hydrogen or a group represented by the formula

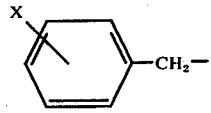

wherein X is as defined above, particularly (1-benzyloxycarbonyl-3-methylbutyl)-penicillin and pharmaceutically acceptable salts thereof. Other preferred compounds in accordance with the present invention include:
   (1-ethoxycarbonyl-3-methylbutyl)-penicillin,
   [1-(5-indanoyloxycarbonyl)-butyl]-penicillin, and
   [3-methyl-1-(pivaloyloxymethoxy-carbonyl)-butyl]-O penicillin and pharmaceutically acceptable salts thereof.

The compounds of formula I and their pharmaceutically acceptable salts can exist as optically pure isomers and as isomeric mixtures, the preferred compounds in accordance with the invention are in the D-form.

In accordance with the present invention, the compounds represented by formula I are prepared by reacting-6-amino- penicillanic acid, the carboxyl group of which is in a protected form, with an acid represented by the formula

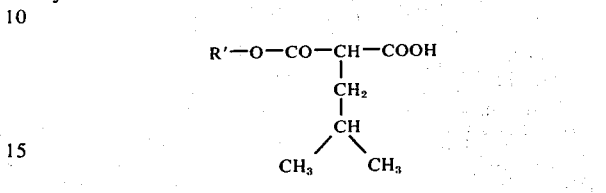

wherein R' represents lower alkanoyloxymethyl, lower alkyl, indanyl or a group represented by the formula

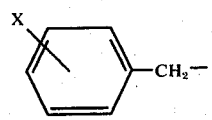

wherein X has the meaning given above,
or with a reactive functional derivative thereof. Such functional derivatives are conventional and include, for example, halides, e.g. chlorides, bromides and fluorides, azides, anhydrides-particularly mixed anhydrides with strong acids, reactive esters such as the N-hydroxysuccinimide esters, amides such as imidazoles and the like. After the reaction is completed, the protecting group is cleaved off and, if desired, the product converted into a salt. Where R in the reaction product of formula represents a group represented by the formula

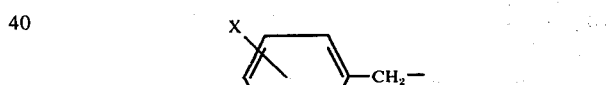

wherein X has the meaning given above
such group may be cleaved off to yield a compound of formula I where R is hydrogen.

Examples of methods whereby the carboxyl of 6-aminopenicillanic acid can be protected include conversion into a readily cleavable ester such as, for example, the benzyl ester, or a silyl ester such as the trimethyl-silyl ester, or by salt formation with an inorganic or tertiary organic base such as, for example, triethylamine. When the condensation of 6-aminopenicillanic acid and the compound represented by formula II is completed, the ester protecting group can be easily removed by methods known in the art. For example, a benzyl ester can be easily removed by catalytic hydrogenation such as, for example, in the presence of a noble metal catalyst such as palladium-on-carbon, and a silyl ester can be cleaved by treating the product with water. Where the carboxyl group of 6-aminopenicillanic acid is protected by salt formation, e.g., with triethylamine, the protecting group can be cleaved by treatment with acids such as, for example, hydrochloric acid, sulfuric acid, phosphoric acid, citric acid and the like at low temperatures, e.g., 0°–5° C.

The reaction of 6-aminopenicillanic acid, having a protected carboxyl group and the compound represented by formula II is carried out by methods well known in the art of peptide chemistry. Thus, for example, the reaction is effected in the presence of a carbodiimide such as, for example dicyclohexylcarbodiimide or an oxazolium salt such as, for example, N-ethyl-5-phenyl-isoxaolium-3'-sulfonate, in an inert solvent. Suitable solvents include, for example, ethyl acetate, acetonitrile, dioxan, chloroform, methylene chloride, benzene, dimethylformamide and the like. In a like manner, a salt of 6-aminopenicillanic acid such as, for example, a trialkylammonium salt, is reacted with a reactive functional derivative of a compound represented by formula II. The reaction of 6-aminopenicillanic acid having a protected carboxyl group and an acid compound represented by forumula II, or a reactive functional derivative thereof, can conveniently be carried out at a temperature between about $-40°$ C and $5°$ C, preferably at about $0°$ C.

After the reaction has been effected, the protecting group is cleaved off. Where the protecting group is a benzyl group (benzyl ester), this can be cleaved off by catalytic hydrogenation (e.g. in the presence of a noble metal catalyst such as palladium/charcoal). When the protecting group is a silyl group (silyl ester), this group can be cleaved off especially readily by treatment of the reaction product with water. Where the carboxyl group of the 6-aminopenicillanic acid is protected by salt formation (e.g. with triethylamine), then the cleavage of this protecting group is carried out by treatment with acid at a proportionately lower temperature (e.g. at about $0°$ C to about $10°$ C). Examples of acids which can be used are hydrochloric acid, sulphuric acid, phosphoric acid or citric acid.

Where it is desired to cleave a benzyl group represented by the formula

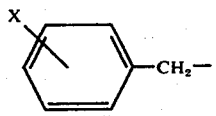

wherein X is as defined above from a compound of formula I wherein R represents said group, such cleavage can expediently carried out, for example, by catalytic hydrogenation, preferably in the presence of a noble metal catalyst such as palladium/charcoal in a polar solvent such as, for example water, a lower alkanol, e.g. isopropanol, or mixtures thereof. The reaction is preferably carried out at a temperature between about $0°$ C and $30°$ C.

The acids of formula II and their reactive functional derivatives are either known compounds or can be prepared by methods conventional in the art. The acids of formula II normally occur as racemates. These racemates can be separated into optically active isomers by processes conventional in the art. For example, the racemates may be reacted with an optically active resolving agent such as, for example, an optically active base, e.g. $\alpha,\alpha$-(1-naphtyl)-ethylamine or $\alpha$-methyl-benzylamine which can react with the carboxyl group. The diastereomers are then separated by selective crystallization and are subsequently converted into the corresponding optical isomers.

The compounds of formula I in the D-form can be prepared by the conventional separation of an isomeric mixture, for example by fractional crystallization of a salt such as the calcium salt, or by utilizing an acid of formula II in the D-form for the above described reaction with 6-aminopenicillanic acid. The latter preparation is preferred.

The compounds of formula I possess a broad spectrum of bacteriocidal activity against both gram-positive and gram-negative microorganisms and can therefore be used both therapeutically and as disinfectants. They have been found to be active against ampicillin-resistant or indole-positive Proteus strains, ampicillin resistant Pseudomonas strains and penicillin resistant Staphylococcus strains.

The compound of formula I wherein R is hydrogen are particularly suited for the treatment of general infections, especially via parenteral administration. A suitable parenteral dosage for adults would be, for example, 5 to 10 g administered from one to four times daily. The compounds of formula I wherein R is other than hydrogen are particularly suited for the therapeutic treatment of infections of the urinary tract. It is preferred to administer these compounds orally, due to their stability in gastric acid, in dosages of up to one gram from one to four times daily. The compounds of formula I may be administered in the form of their pharmaceutical acceptable salts or hydrates of such salts.

Examples of the pharmaceutically acceptable salts of the penicillin compounds represented by formula I include salts with inorganic bases such as, for example, the alkali metal salts, e.g., the sodium or potassium salt; ammonium salts; alkaline earth metal salts e.g., the calcium salt and the like; and salts with organic bases such as amine compounds for example, N-ethyl piperidine, procaine, dibenzylamine, N,N'-dibenzylethylthylenediamine, alkylamines, dialkylamines or the like. The foregoing salts can also be hydrated. The hydration can be effected during the manufacturing process or can occur gradually as a consequence of the hygroscopic properties of an initially anhydrous salt.

The antimicrobial activity of representative compounds falling within the scope of the present invention is set forth in the following table.

TABLE

| Compounds | Mode of Administration | CD$_{50}$ (mg/kg) in the mouse | | | Proteus Vulganis | Acute Toxicity mg/kg Mode of Administration) |
| --- | --- | --- | --- | --- | --- | --- |
| | | Escherichia coli | Pseudomonas Aeriginmos | S. aureous (penicillin resistant) | | |
| (1-ethoxycarbonyl-3-methylbutyl)-penicillin sodium | P.O. | 14 | ca 100 | ca 100 | — | 2000–4000 (i.v.) |
| | S.C. | 2.1 | ca 80 | 22 | — | 5000 (p.o. and s.c.) |
| (1-benzyloxy-carbonyl-3-methylbutyl)-penicillin sodium | P.O | 9 | 142 | — | 8.9 | 2500–5000 (p.o.) |
| (1-carboxy-3-methyl-butyl)-penicillin | S.C. | 2.4 | 124 | 34 | 6.2 | 2000–4000 (i.v.) |

TABLE-continued

| Compounds | Mode of Administration | CD$_{50}$ (mg/kg) in the mouse | | S. aureus (penicillin resistant) | Proteus Vulganis | Acute Toxicity mg/kg Mode of Administration) |
|---|---|---|---|---|---|---|
| | | Escherichia coli | Pseudomonas Aeriginmos | | | |
| sodium | | | | | | |

For purposes of administration, the novel 6-acyl derivatives of 6-aminopenicillanic acid of the present invention can be combined with conventional compatible organic or inorganic pharmaceutical carrier materials known in the art. Such materials include, for example, water, gelatin, gums, lactose, starches, magnesium stearate, talc, vegetable oils, polyalkylene glycols, petroleum jelly and the like. Such pharmaceutical preparations may be in unit dosage form and may additionally contain other therapeutically valuable substances or conventional pharmaceutical adjuvants such as preservatives, stabilizing agents, wetting agents, emulsifying agents, buffers and the like. The pharmaceutical preparations can be in conventional solid dosage forms such as tablets, capsules, dragees and the like, conventional semi-solid forms such as ointments and creams, conventional liquid forms such as solutions, suspensions, emulsions and the like and other conventional dosage forms such as dry ampules, suppositories and the like. Such preparations may be submitted to conventional pharmaceutical expedients such as, for example, sterilization and the like.

The following Examples illustrate the present invention, all temperatures are in degrees centigrade.

EXAMPLE 1

A solution of 23 g of sodium in 1500 ml of anhydrous alcohol was treated, with stirring, with 160.16 g of malonic acid diethyl ester. After stirring for 30 minutes, 184.03 g of isobutyl iodide were added dropwise to the solution. The mixture was then stirred for and additional further 15 hours at 20° and subsequently evaporated under reduced pressure. The residue was stirred with diethyl ether, filtered off from the solid material and evaporated under reduced pressure. The brown oil remaining as the residue was fractionated twice in a high vacuum. There was obtained 45.8 g of a main fraction of isobutylmalonic acid diethyl ester, boiling point 64°/0.6 mm Hg.

A total of 21.6 g of isobutylmalonic acid diethyl ester prepared above was dissolved in 100 ml of ethanol and treated dropwise at 0° with a solution of 5.6 g of potassium hydroxide in 100 ml of ethanol. The solution was allowed to stand to neutral pH for 17 hours at 20° and then evaporated under reduced pressure. The residue was dissolved in ice-water and extracted three times with ethyl acetate. The ethyl acetate extracts were rejected. The aqueous phase was acidified with 2-N hydrochloric acid and extracted twice with ethyl acetate. The combined ethyl acetate extracts were washed once with water, dried over magnesium sulfate and evaporated under reduced pressure. There were obtained 15.3 g of colorless isobutylmalonic acid monoethyl ester in the form of a chromatographically pure oil.

(1-[ethoxycarbonyl-3-methylbutyl)]-penicillin sodium.

5.66 grams of isobutylmalonic acid monoethyl ester were dissolved in 100 ml of anhydrous benzene and treated at 0° with 30 drops of dimethylformamide and 5.14 ml of oxalyl chloride. The mixture was stirred for 1 hour at 0° to 5° and for 30 minutes at 20°. the mixture was evaporated under reduced pressure and the residure re-evaporated once with anhydrous benzene. 6.5 grams of a yellow oil was obtained, which were dissolved in 25 ml of acetone and added dropwise at 0° over a period of 30 minutes to a solution of 6.5 g of 6-aminopenicillanic acid and 8.3 ml of triethylamine. The mixture was then stirred for 1 hour at 0°–5° and subsequently for 1 hour at 20°. After evaporation under reduced pressure, the residue was taken up in water at 0°, adjusted to pH 2–3 with 1-N sulfuric acid and extracted twice with ethyl acetate. The combined ethyl acetate extracts were washed with water, dried over magnesium sulfate and evaporated under reduced pressure. The residue was dissolved in diethyl ether and treated with 15 ml of a 2-N solution of the sodium salt of 2-ethylcaproic acid in ethyl acetate. After dilution with petroleum ether, the precipitate formed was filtered off under vacuum, washed with petroleum ether and dried at 20° under reduced pressure. There was obtained 8.2 g of the sodium salt of (1-ethoxycarbonyl-3-methylbutyl)-penicillin in the form of a white powder; melting point above 100° (decomposition); $[\alpha]_D^{20} = +226.0°$ (C = 1.113 in water).

EXAMPLE 2

A total of 32 g of isobutylmalonic acid was boiled under reflux with 60 g of 5-indanol and 60 g of phosphorus pentoxide in 1000 ml of toluene. The solution was decanted from undissolved material and evaporated under reduced pressure. The brownish oily residue was chromatographed on a column of silica gel with benzene as the eluant. After evaporation under reduced pressure, the fractions containing the desired compound yielded 26.0 g of a light oil which crystallizes on standing to yield isobutylmalonic acid di-5-indanyl ester.

To a solution of 20.3 g of the isobutylmalonic acid di-5-indanyl ester formed above in 300 ml of tert.-butanol there were added 6.25 g solid potassium tert.-butylate. As soon as the latter dissolved, 1.5 ml of water were added to the mixture. The mixture was stirred for 20 hours at 20° and then evaporated under reduced pressure. The residue was partitioned between water and ethyl acetate. According to thin-layer analysis, the desired compound was present as the potassium salt together with 5-indanol in the ethyl acetate phase. The latter was dried over magnesium sulfate and evaporated under reduced pressure, which produces 23 g of oily residue. To separate the 5-indanol, this residue was then added to a column of silica gel and eluted with benzene until no more 5-indanol was dectectable (by means of thin-layer analysis) in the eluate. The desired compound was then eluted as the potassium salt using ethyl acetate as the eluant. After evaporation of this eluate under reduced pressure, there were obtained 7.5 g of residue as hygroscopic particles. The latter were dissolved in ethyl acetate and the solution shaken out with ice-cold 1-N hydrochloric acid. The ethyl acetate phase was then washed with water dried over sodium sulfate and evaporated under reduced pressure. There were obtained 6.8 g of pure isobutylamonic acid mono-5-indanyl ester in the form of a light-brown oil.

[1-(5-Indanyloxy-carbonyl)-3-methylbutyl]-penicillin sodium.

5.85 grams of isobutylmalonic acid mono-5-indanyl ester formed above were treated at 0° in 100 ml of anhydrous benzene with 20 drops of dimethylformamide and 3.64 ml of oxalyl chloride. The mixture was stirred for 1 hour at 0° and for 30 minutes at 20° and then evaporated under reduced pressure. The residue was then twice re-evaporated with benzene. The orange-red oil thus obtained was dissolved in 50 ml of acetone and added dropwise at 0° during 30 minutes to a solution of 4.58 g of 6-aminopenicillanic acid and 5.9 ml of triethylamine in 100 ml of methylene chloride. The mixture was stirred for 1 hour at 0° and for 1 hour at 20° and then evaporated under reduced pressure. The residue was dissolved in ice-water, acidified to pH 2-3 with 1-N hydrochloric acid and extracted twice with ethyl acetate. The combined ethyl acetate extracts were washed with water, dried over magnesium sulfate and evaporated under reduced pressure. The foamy residue was dissolved in diethyl ether and treated with 10.6 ml of a 2-N solution of the sodium salt of 2ethylcaproic acid in ethyl acetate. After dilution with petroleum ether, the precipitate was filtered off under vacuum, rinsed with petroleum ether and dried at 20° under reduced pressure. There were obtained 7.0 g of the sodium salt of [1-(5-indanyloxycarbonyl)-3-methylbutyl]-penicillin in the form of a beige powder; melting point above 100° (decomposition); $[\alpha]_D^{20} = +191.5°$ (c = 1.94 in ethanol).

EXAMPLE 3

A total of 334. 75 g of malonic acid dibenzyl ester was dissolved in 1310 ml of dimethylformamide and treated in portions with 51.5 g of 55% sodium hydride which has been previously decanted once with anhydrous benzene. The mixture was stirred for 1.5 hours and then 241 g of isobutyl iodide added dropwise. After stirring for 65 hours, the mixture was evaporated under reduced pressure and the residue stirred with diethyl ether. After filtration of undissolved material, the diethyl ether solution was washed three times with water, dried over magnesium sulfate and evaporated under reduced pressure. The oily residue obtained was distilled twice in a high vacuum, which yields 314 g of pure isobutylmalonic acid dibenzyl ester as a light-yellow oil, boiling point 185°–188°/0.6 mm Hg.

In a manner analogous to Example 2 by monosaponification of isobutylmalonic acid dibenzyl ester with 1 equivalent of potassium tert.-butylate/water in tert.-butanol there was obtained isobutylmalonic acid monobenzyl ester in 56.3% yield as a pure colorless oil.

35.6 grams of the isobutylmalonic acid monobenzyl ester thus-obtained were dissolved in 300 ml of dimethylformamide and treated portionwise at 20° with 6.2 g of 55% sodium hydride which has been previously decanted once with anhydrous benzene. The mixture was then stirred for 30 minutes at 20°. Subsequently, 25.5 g of pivaloyloxymethyl chloride were added dropwise during 30 minutes at 20° and the mixture stirred for 72 hours at 20°. After treatment with a small amount of methanol (to decompose any unreacted sodium hydride), the mixture was poured into water. After the addition of diethyl ether, the mixture was extracted twice with a 10% sodium bicarbonate solution. The sodium bicarbonate extracts were rejected. The diethyl ether phase was washed once with water, dried over magnesium sulfate and evaporated under reduced pressure. There were obtained 50 g of a yellow oil, which is chromatographed on a silica gel column using benzene as the eluant. There were obtained 34.6 g of pure isobutylmalonic acid benzyl ester pivaloyloxymethyl ester in the form of a colorless oil.

34.6 grams of isobutylmalonic acid benzyl ester pivaloyloxymethyl ester were dissolved in 150 ml of dimethylformamide and hydrogenated with 3.0 g of 5% palladium/charcoal. After 1 hour, the hydrogen uptake (2160 ml) had finished. The hydrogenation mixture was filtered off from the catalyst and the filtrate evaporated in a high vacuum at room temperature. The oily residue was dissolved in a 10% aqueous sodium bicarbonate solution and extracted twice with diethyl ether. The diethyl ether extracts were rejected. The sodium bicarbonate phase was acidified at 0° with citric acid and extracted twice with diethyl ether. The combined diethyl ether extracts were washed once with water, dried over magnesium sulfate and evaporated under reduced pressure. There was obtained 21.5 g of pure isobutylmalonic acid mono-pivaloyloxymethyl ester in the form of a colorless oil.

[3-methyl-1-(pivaloyl-oxymethoxycarbonyl)-butyl]-penicillin sodium.

A total of 4.8 g of the isobutylmalonic acid monopivaloyloxymethyl ester formed above was treated at 0° in 50 ml of benzene with 17 drops of dimethylformamide and 3.0 ml of oxalyl chloride. The mixture was stirred for 1 hour at 0° and for 30 minutes at 20°, subsequently evaporated under reduced pressure and re-evaporated twice with benzene. The residue as a yellow oil was dissolved in 50 ml of acetone and added dropwise at 0° during 50 minutes to a solution of 3.78 g of 6-aminopenicillanic acid and 4.85 ml of triethylamine in 50 ml of methylene chloride. The mixture was stirred for 1 hour at 0° and for 1 hour at 20° and then evaporated under reduced pressure. The residue was dissolved in ice-water, acidified to pH 3 with citric acid and extracted twice with ethyl acetate. The combined ethyl acetate extracts were washed with water, dried over magnesium sulfate and evaporated under reduced pressure. There were obtained 8 g of foamy residue, which is dissolved in 100 ml of diethyl ether and treated with 9 ml of a 2-N solution of the sodium salt of 2-ethylcaproic acid in ethyl acetate. The resulting solution was poured into 2 liters of low-boiling petroleum ether. The precipitate was filtered off under vacuum and washed with low-boiling petroleum ether. After reprecipitation from ether/low-boiling petroleum ether and drying at 20° C under reduced pressure, there were obtained 5.2 g of the sodium salt of [3-methyl-1-(pivaloyloxymethoxy-carbonyl)-butyl]-penicillin in the form of a yellowish powder; melting point above 100° (decomposition); $[\alpha]_D^{20} = +160°$ (c = 0.987 in ethyl acetate).

EXAMPLE 4

128 grams of malonic acid dibenzyl ester were dissolved in 500 ml of dimethylformamide and treated carefully in portions with 21.6 g of 50% sodium hydride which has been decanted once with absolute benzene. After stirring at 20° for 1.5 hours, 92 g of isobutyl iodide were added dropwise to the mixture. After stirring at 20° for a further 65 hours, the mixture was evaporated under reduced pressure. The residue was stirred with ether, filtered off from undissolved material and the ethereal solution washed three times with water, dried over magnesium sulfate and evaporated under reduced pressure. After distillation of the residue under a high vacuum, there were obtained 125 g (79% of theory) of isobutyl malonic acid dibenzyl ester as a practically colorless oil of boiling point 175°/0.4 Torr.

23.9 grams of isobutylmalonic acid dibenzyl ester were dissolved in 80 ml of benzyl alcohol and treated dropwise at 0° with a solution of 3.69 g (previously finely powdered in a mortar) of potassium hydroxide in 80 ml of benzyl alcohol. The mixture was left to stand to a neutral pH for 20 hours at 20°. After evaporation under high vacuum, the residue was dissolved in icewater and extracted 3 times with ethyl acetate (these ethyl acetate extracts were rejected). The aqueous phase was acidified with 2-N hydrochloric acid and extracted twice with ethyl acetate. The combined ethyl acetate extracts were washed once with water, dried over magnesium sulfate and evaporated under reduced pressure. There were obtained 13.7 g of a light-yellow oil which for purification was chromatographed on a silica gel column (0.2–0.5 mm) using ethyl acetate as the eluant. There was obtained 10.0 g of isobutylmalonic acid monobenzyl ester as a pure colorless oil with a Rf value of 0.58 (thin-layer chromatography on silica gel plates using ethyl acetate as the eluant).

9.7 grams of the thus-obtained isobutylmalonic acid monobenzyl ester were dissolved in 120 ml of absolute benzene. The solution was treated with 40 drops of dimethylformamide and subsequently, at 0°, with 6.64 ml of oxalyl chloride. After stirring at 0°–5° for 1 hour and for 30 minutes at 20°, the mixture was evaporated under reduced pressure and the residue re-evaporated once with benzene to yield isobutylmalonic acid monobenzyl ester chloride as an orange-red oil.

(1-benzyloxycarbonyl-3-methylbutyl)-penicillin sodium.

A solution of the isobutylmalonic acid monobenzyl ester chloride obtained above in 50 ml of acetone was added dropwise at 0° during 30 minutes to a solution of 8.38 g of 6-amino-penicillanic acid and 10.7 ml of triethylamine in 120 ml of methylene chloride. The mixture was then stirred for 1 hour at 0° and for 1 hour at 20°. After evaporation under reduced pressure, the residue was partitioned between ice-water and ethyl acetate, acidified with 1-N sulfuric acid and extracted twice with ethyl acetate. The combined ethyl acetate extracts were washed with water, dried over magnesium sulfate and evaporated under reduced pressure. The residue was dissolved in ether and treated with 20 ml of a 2-N 2-ethylcaproic acid sodium salt solution in ethyl acetate. The penicillin salt was precipitated with petroleum ether, filtered off under vacuum, washed with petroleum ether, filtered off under vacuum, washed with petroleum ether and dried at 20° under a high vacuum. There are obtained 12.6 g (69% of theory) of the sodium salt of (1-benzyloxycarbonyl-3-methylbutyl)-penicillin as a light-beige powder of melting point 80° (decomposition); $[\alpha]_D^{20} = +194°$ [c = 0.512 in water/ethanol (1:1)]. EXAMPLE 5

(1-Carboxy-3-methyl-butyl)-penicillin di-sodium.

4.7 grams of a 10% palladium on charcoal catalyst were first pre-hydrogenated in 50 ml of isopropanol, 80 ml of hydrogen being taken up. To the resulting catalyst suspension there was then added a solution of 4.7 g of the sodium salt of (1-benzyloxycarbonyl-3-methylbutyl)-penicillin in a mixture of 90 ml of isopropanol and 10 ml of water. The mixture was hydrogenated. After a hydrogen uptake of 145 ml within 100 minutes, the hydrogenation came to a premature standstill because of catalyst poisoning. The catalyst was filtered off, rinsed with isopropanol and water and the filtrate evaporated under reduced pressure. The residue was dissolved in 70 ml of isopropanol/water (9:1) and hydrogenated again with 4.7 g of 10% palladium on charcoal catalyst, 155 ml of hydrogen being taken up in 100 minutes. The hydrogenation was then discontinued. After filtration of the catalyst and rinsing with isopropanol, the filtrate was evaporated under vacuum. The residue was treated with ethyl acetate, filtered off under vacuum and washed with petroleum ether. There were obtained 2.45 g of the monosodium salt as a bright-yellow powder which, for conversion to the desired disodium salt, was dissolved in 50 ml of water and treated with 510 mg of sodium bicarbonate. The solution was stirred for 10 minutes at 25° and then evaporated at 25° under vacuum. The residue was re-evaporated with ethyl acetate. There were obtained 2.52 g (63% of theory) of the pure disodium salt of (1-carboxy-3-methyl-butyl)-penicillin as a bright-yellow powder of melting point 240° (decomposition); $[\alpha]_D^{20} = +174.6°$ [c = 0.528 in water/ethanol (1:1)].

EXAMPLE 6

[1-(p-Chlorobenzyl)-oxycarbonyl-3-methylbutyl]-penicillin sodium.

16.4 grams of isobutylmalonic acid mono-(p-chlorobenzyl) ester were dissolved in 100 ml of benzene and 40 ml of oxalyl chloride at room temperature with the addition of 2 drops of dimethyl-formamide. After 2 hours, the mixture was concentrated and the oily residue re-evaporated three times with benzene. The acid chloride was dissolved in 50 ml of methylene chloride and added at 0° to a solution of 7.9 g of 6-aminopenicillanic acid in 100 ml of methylene chloride and 15.3 ml of triethylamine. After 2 hours, the mixture was evaporated to dryness. The residue was dissolved in water, washed with ether and acidified to pH 2.5 with citric acid. The separated acid was taken up in ethyl acetate and the solution washed with water, dried and concentrated. The residue was dissolved in ether and the sodium salt precipitated by the addition of 14 ml of a 2-N solution of 2-ethylcaproic acid sodium salt in ethyl acetate. The product is filtered off and dried. There were obtained 12.0 g (65% of theory) of the sodium salt of [1-(p-chlorobenzyl)oxcarbonyl-3-methybutyl]-penicillin as a white powder of melting point 125°; $[\alpha]_D^{25} = +193°$ (c = 1 in water).

EXAMPLE 7

The following composition was prepared as follows and filled into gelatin capsules.

| Ingredients | Amount per capsule |
| --- | --- |
| [1-(5-Indanyloxy)-carbonyl-3-methylbutyl]-penicillin sodium | 1052 mg |
| Luviskol' (trademark — a water-soluble polyvinyl-pyrrolidone) | 46 mg |
| Mannitol | 40 mg |
| Talc | 38 mg |
| Magnesium stearate | 4 mg |

| Ingredients | Amount per capsule |
|---|---|
| Total | 1180 mg |

1. A water-soluble polyvinyl pyrrolidone manufactured by Badische Anilin U. Sodafabrid Ludwigshafen am Rhein, German Federal Republic.

The penicillin was homogeneously blended with the Luviskol and Mannitol and compressed into slugs. The slugs were then passed through a suitable sieving machine and after blending with the talk and magnesium stearate, filled into capsules.

EXAMPLE 8

Suitable gelatin capsules were filled with the following composition in the manner described in Example 7.

| | Amount |
|---|---|
| (1-Benzyloxycarbonyl-3-methylbutyl)-penicillin sodium | 1000 mg |
| Luviskol | 46 mg |
| Mannitol | 40 mg |
| Talc | 38 mg |
| Magnesium stearate | 4 mg |
| Total | 1128 mg |

EXAMPLE 9

Reconstitutable injectable preparations were prepared by lyophilizing and hermetically sealing ampoules each containing 2 ml of a sterile solution containing 789 mg of [1-(ethyoxycarbonyl)-3-methylbutyl]-penicillin sodium, 1.1. mg. of methyl-p-hydroxybenzoate and 0.135 mg of propyl-hydroxybenzoate.

I claim:

1. Compounds represented by the formula

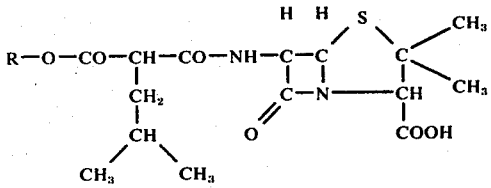

wherein R is represented by the formula

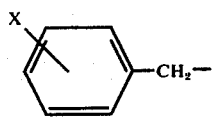

wherein X is hydrogen, halogen, hydroxy, lower alkyl, lower alkoxy or lower alkoxy-lower alkyl and pharmaceutically acceptable salts and hydrated forms thereof.

2. Compounds in accordance with claim 1 which have the D configuration.

3. A compound in accordance with claim 1 wherein X is hydrogen, i.e. the compound (1-benzyloxycarbonyl-3-methyl-butyl)-penicillin.

4. A compound in accordance with claim 3 wherein said pharmaceutically acceptable salt is the sodium salt.

* * * * *

UNITED STATES PATENT AND TRADEMARK OFFICE
CERTIFICATE OF CORRECTION

PATENT NO. : 4,005,073　　　　　　　　　　　　　　　Page 1 of 2
DATED : January 25, 1977
INVENTOR(S) : Roland Reiner It is certified that error appears in the above-identified patent and that said Letters Patent are hereby corrected as shown below:

Column 12, claim 1, lines 6-14

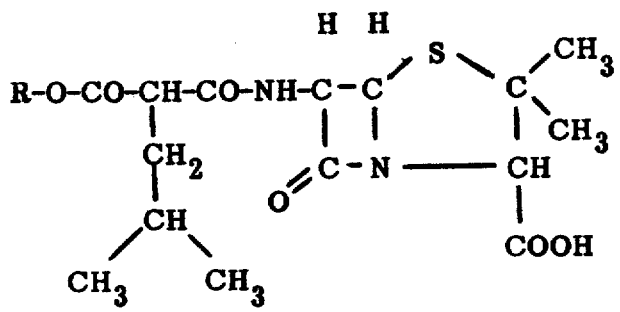

should be:

UNITED STATES PATENT AND TRADEMARK OFFICE
CERTIFICATE OF CORRECTION

PATENT NO. : 4,005,073

DATED : January 25, 1977

INVENTOR(S) : Roland Reiner

It is certified that error appears in the above–identified patent and that said Letters Patent are hereby corrected as shown below:

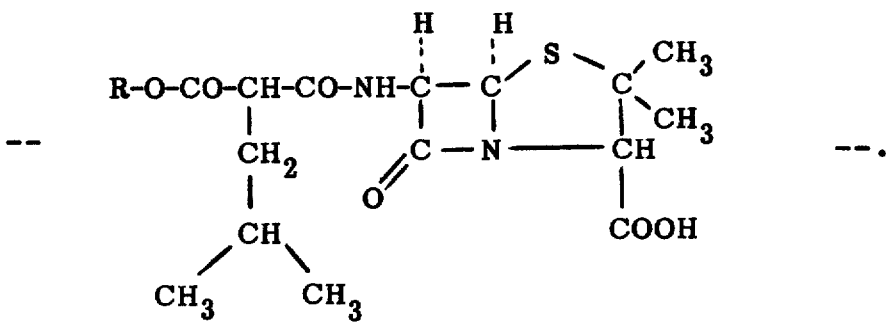

Signed and Sealed this

Twenty-seventh Day of November 1979

[SEAL]

Attest:

RUTH C. MASON
*Attesting Officer*

LUTRELLE F. PARKER
*Acting Commissioner of Patents and Trademarks*